United States Patent [19]
Anagnostopulos et al.

[11] Patent Number: 5,958,413
[45] Date of Patent: Sep. 28, 1999

[54] USE OF ANTIBODIES TO TNF OR FRAGMENTS DERIVED THEREOF AND XANTHINE DERIVATIVES FOR COMBINATION THERAPY AND COMPOSITIONS THEREFOR

[75] Inventors: Hiristo Anagnostopulos, Wiesbaden; Ulrich Gebert, Glashutten; Heinz Hanel, Oberursel; Michael Limbert, Hofheim, all of Germany; Mark William Bodmer, South Hinksey; Gerald Anthony Higgs, London, both of United Kingdom

[73] Assignees: Celltech Limited, Berkshire; Hoechst Aktiengesellschaft, Frankfurt, both of Germany

[21] Appl. No.: 08/966,544

[22] Filed: Nov. 10, 1997

Related U.S. Application Data

[62] Continuation of application No. 08/378,261, Jan. 26, 1995, abandoned, which is a continuation of application No. 08/039,316, filed as application No. PCT/GB91/01907, Oct. 30, 1991, abandoned.

[51] Int. Cl.$^6$ ................ A61K 39/395; A61K 45/05; C07K 16/00; A01N 43/90
[52] U.S. Cl. ................ 424/178.1; 424/181.1; 424/85.1; 530/387.1; 530/388.23; 514/263; 514/929
[58] Field of Search ................ 514/263, 929; 424/85.1, 88, 178.1, 181.1; 530/387.1, 388.23

[56] References Cited

U.S. PATENT DOCUMENTS

| | | | |
|---|---|---|---|
| 4,748,018 | 5/1988 | Stolle et al. | 424/87 |
| 4,965,271 | 10/1990 | Mandell et al. | 514/263 |
| 5,118,500 | 6/1992 | Hänel et al. | 424/85.1 |

FOREIGN PATENT DOCUMENTS

| | | |
|---|---|---|
| 0 171 496 | 2/1986 | European Pat. Off. . |
| 0 173 494 | 3/1986 | European Pat. Off. . |
| 0 239 400 | 9/1987 | European Pat. Off. . |
| 0 344 586 | 12/1989 | European Pat. Off. . |
| 0351789 | 1/1990 | European Pat. Off. . |
| 86/01533 | 3/1986 | WIPO . |
| 89/01782 | 3/1989 | WIPO . |
| 89/01950 | 3/1989 | WIPO . |
| 89/01974 | 3/1989 | WIPO . |
| 89/02465 | 3/1989 | WIPO . |
| 89/08460 | 9/1989 | WIPO . |
| WO 90/01950 | 3/1990 | WIPO . |

OTHER PUBLICATIONS

Goldstein et al., Clinics in Chest Medicine., vol. 11., No. 4., Dec. 1990.

Beutler et al., "Passive Immunization Against Cachectin/Tumor Necrosis Factor Protects Mice from Lethal Effect of Endotoxin", Science, vol. 229, Aug. 1985, pp. 869–871.

Piguet et al., "Tumor Necrosis Factor/Cachectin is an Effector of Skin and Gut Lesions of the Acute Phase of Graft–vs–Host Disease", J. Exp. Med., vol. 166, Nov. 1987, pp. 1280–1289.

Shalaby et al., "Prevention of the Graft–versus–Host Reaction in Newborn Mice by Antibodies to Tumor Necrosis Factor–Alpha", Transplantation, vol. 47, No. 6, Jun. 1989, pp. 1057–1061.

Boorebaeck, Journal of Immunological Methods, vol. 123, pp. 157–165, (1989).

Parham, "On the Fragmentation of Monoclonal lgG1, lgG2a, and lgG2b from BALB/c Mice", Journal of Immunology, vol. 131, No. 6, Dec. 1983, pp. 2895–2902.

Lamoyi et al., "Preparation of F(ab')$_2$ Fragments from Mouse lgG of Various Subclases", Journal of Immunology Methods, vol. 56, 1983, pp. 235–243.

Koehler et al., "Derivation of Specific Antibody–Producing Tissue Culture and Tumor Lines by Cell Fusion", Eur. J. Immunol., vol. 6, 1976, pp. 511–519.

Tracey et al., "Anti–Cachectin/TNF Monoclonal Antibodies Prevent Septic Shock During Lethal Bacteraemia", Nature, vol. 330, Dec. 1987, pp. 662–664.

Strieter et al., "Cellular and Molecular Regulation of Tumor Necrosis Factor–Alpha Production by Pentoxifylline", Biochemical and Biophysical Research Communications, vol. 155, No. 3, 1988, pp. 1230–1236.

Lilly et al., "Pentoxyfylline Prevents Hypotension and Pulmonary Injury Caused by Tumor Necrosis Factor", American Review of Respiratory Disease, vol. 137, No. 4, part 2, Apr. 1988, p. 138, Abstract.

Waldmann, Science, vol. 252, pp. 1657–1662, (1991).

Sevier et al., Clin. Chem., vol. 27, No. 11, pp. 1797–1806, (1981).

Biotechnology Newswatch, pp. 2–3, Oct. 4, 1993.

Dillman, Annals of Internal Medicine, vol. 111, No. 7, pp. 592–603, (1989).

U.S. News & World Report, p. 13, Aug. 1, 1994.

Norick et al. Biorheology, 27; 449–454, 1990.

*Primary Examiner*—Ponnathapura Achutamurthy
*Assistant Examiner*—P. Ponnaluri
*Attorney, Agent, or Firm*—Foley & Lardner

[57] ABSTRACT

A combined preparation for simultaneous combined, simultaneous separate, or sequential use in the therapy of prophylaxis of disorders associated with undesirable high levels of TNF, e.g. septic or endotoxic shock and immunoregulatory and inflammatory disorders, which comprises an antibody to TNF or a TNF binding fragment thereof and a xanthine derivative. Particular preferred xanthine derivatives are 3,7-dimethyl-1(5-oxo-hexyl)xanthine (known as Pentoxifylline or TRENTAL) and 1-(5-hydroxy-5-methylhexyl)-3-methylxanthine and similar compounds. The anti-TNF antibody or fragment is preferably monospecific especially a humanized recombinant antibody or fragment.

23 Claims, 5 Drawing Sheets

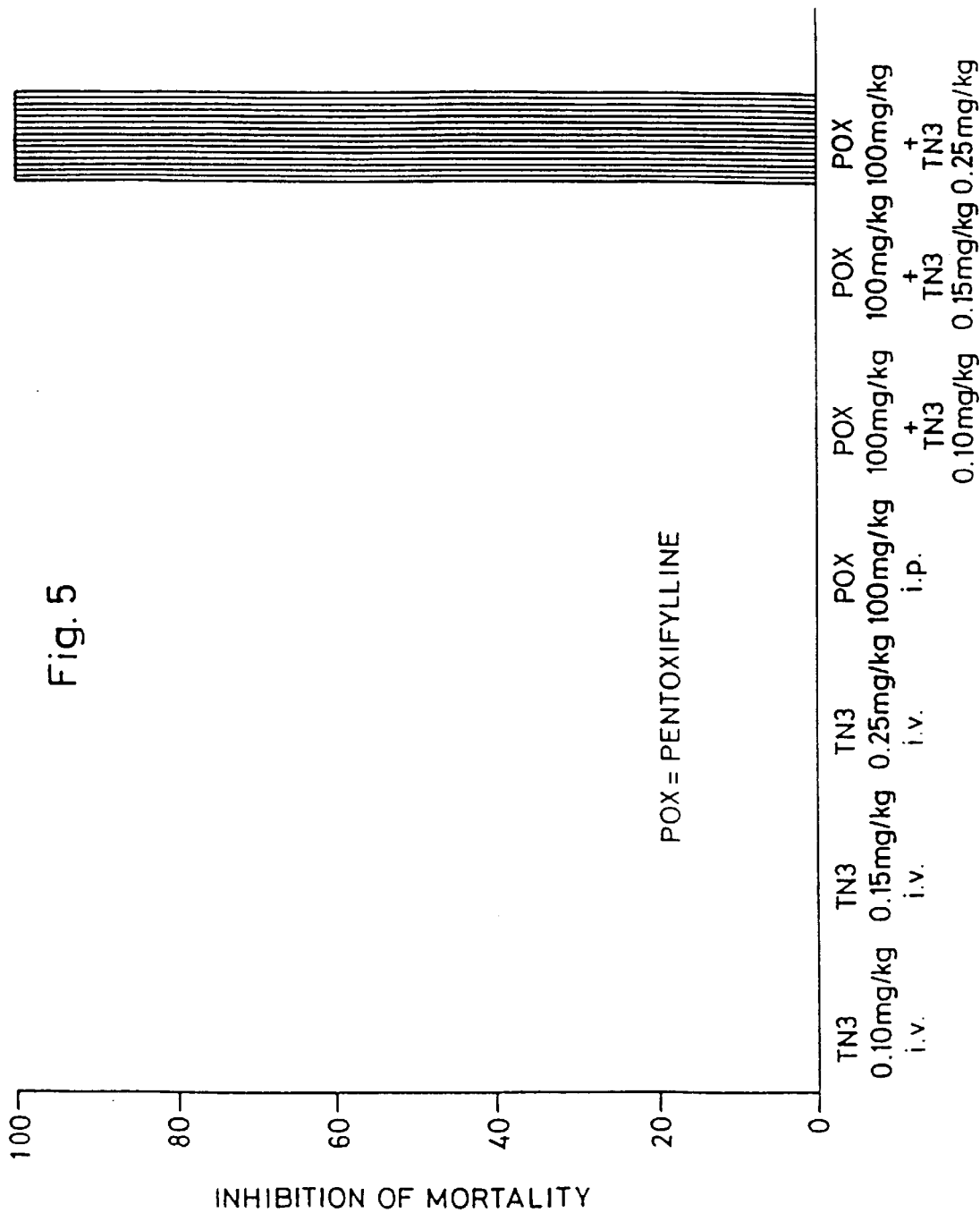

USE OF ANTIBODIES TO TNF OR FRAGMENTS DERIVED THEREOF AND XANTHINE DERIVATIVES FOR COMBINATION THERAPY AND COMPOSITIONS THEREFOR

This application is a continuation application of Ser. No. 08/378,261, filed Jan. 26, 1995, now abandoned which is a continuation of Ser. No. 08/039,316, filed Jul. 22, 1993, now abandoned, which is the National Phase of PCT/GB91/01907, filed Oct. 30, 1991.

FIELD OF THE INVENTION

The present invention relates to a pharmaceutical product for the treatment of conditions associated with elevated levels of tumour necrosis factor-α (herein referred to as TNF) and to the manufacture of such a product. The pharmaceutical product may, for example, be employed in the treatment of sepsis, and, in particular in the treatment of septic, or endotoxic shock.

BACKGROUND TO THE INVENTION

TNF is a cytokine which is produced by activated macrophage and other cells and is an important regulator in inflammation and immunity. It is implicated in septic shock—an often fatal condition associated with Gram-negative or Gram-positive bacteremia—as well as in other conditions such as adult respiratory distress syndrome, graft-versus-host disease and auto-immune diseases.

Treatments of these conditions involving the use of antibodies to TNF (anti-TNF antibodies) have been proposed and tested. For example, Beutler et al (Science (1985), 229, 869–871) showed that passive immunisation with a rabbit polyclonal antiserum against TNF protected mice from the lethal effects of Gram-negative endotoxin. Similarly, antibody therapy against TNF has been shown to decrease mortality in mice undergoing graft-versus-host disease (GVHD) and to prevent splenomegaly, and cutaneous and intestinal lesions associated with acute phase GVHD. (Piguet, P. F., et al, J. Exp. Med. 1987; 166: 1280; Shalaby, M. R., et al, Transplantation 1989; 47: 1057).

In addition, patent applications of Celltech Limited disclose the use of anti-TNF antibodies in the amelioration of side effects associated with anti-lymphocyte therapy of graft-rejection (WO89/08460), and with anti-neoplastic chemotherapy (WO89/01950).

Certain xanthine derivatives are also known to be inhibitors of TNF. For example, EP-A-0344586 of Hoechst Aktiengesellschaft discloses xanthine derivatives effective in inhibiting the TNF whose release is induced by certain TNF-releasing substances such as amphoterocin B.

The present inventors have observed that in some experimental models of septic shock a surprising combination effect is produced if an antibody to TNF and a xanthine derivative are used in combination.

SUMMARY OF ASPECTS OF THE INVENTION

Thus, according to a first aspect of the present invention there is provided a pharmaceutical product comprising an antibody to TNF or a TNF binding fragment thereof and a xanthine derivative as a combined preparation for simultaneous combined, simultaneous separate, or sequential use in therapy.

Such a pharmaceutical product may take the form of a pharmaceutical composition in which the antibody to TNF, or TNF binding fragment thereof and the xanthine derivative occur in admixture, optionally together with a pharmaceutically acceptable excipient, diluent, or carrier.

The ratio by weight of xanthine derivative to anti-TNF antibody in the composition may vary between 450:1 and 1:10; preferably it is in the range 150:1–1:5 and particularly preferably between 30:1 and 1:2 for example 1:1.

Suitable xanthine derivatives for inclusion in the pharmaceutical product of the present invention include the following:

1) Compounds of the formula I

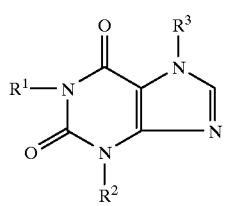

(I)

in which one of the radicals $R^1$ and $R^3$ represents a straight-chain alkyl, (ω-1)-oxoalkyl or (ω-1)-hydroxyalkyl group having 3 to 8 carbon atoms, and the two other radicals, $R^2$ and $R^3$ or $R^1$ and $R^2$, represent straight-chain or branched alkyl groups having 1 to 8 carbon atoms in the position of $R^1$ and $R^3$ and 1 to 4 carbon atoms in the position of $R^2$, where the total of carbon atoms in these two alkyl substituents does not exceed 10;

2) Compounds of the formula II

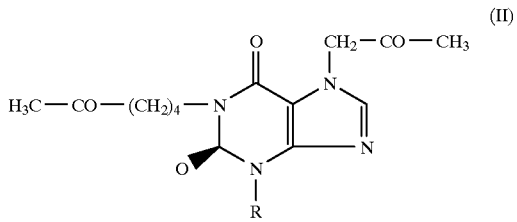

(II)

in which R represents an alkyl radical having 1 to 4 carbon atoms;

3) Compounds of the formula III

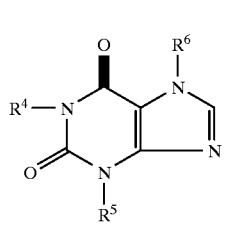

(III)

in which at least one of the radicals $R^4$ and $R^6$ represents a tertiary hydroxyalkyl group of the formula

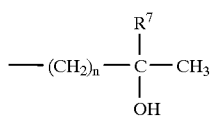
(IIIa)

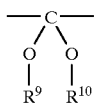
(IV)

where $R^7$ denotes an alkyl croup having up to 3 carbon atoms, and n denotes an integer from 2 to 5, and—if only one of the radicals $R^4$ or $R^6$ denotes such a tertiary hydroxyalkyl group of the formula IIIa—the other radical represents a hydrogen atom or an aliphatic hydrocarbon radical $R^8$ which has up to 6 carbon atoms and whose carbon chain can be interrupted by up to 2 oxygen atoms or substituted by an oxo group or up to two hydroxyl groups (in which case an oxo or hydroxyl group present in the radical $R^8$ is preferably separated from the nitrogen by at least 2 carbon atoms), and $R^5$ represents an alkyl group having 1 to 4 carbon atoms;

4) Prodrug forms of the compounds of the formulae I to III, and/or

5) Metabolites of the compounds of the formulae I to III.

In particularly preferred embodiments the xanthine derivative is of formula I with a hexyl, 5-oxohexyl or 5-hydroxyhexyl group in the position of $R^1$ or $R^3$. For example, 1-hexyl-3,7-dimethylxanthine, 1-(5-hydroxyhexyl)-3,7-dimethylxanthine, 3,7-dimethyl-1-(5-oxohexyl)xanthine, 7-(5-hydroxyhexyl)-1,3-dimethylxanthine, 1,3-dimethyl-7-(5-oxohexyl)xanthine, 1,3-di-n-butyl-7-(2-oxopropyl or 3-oxobutyl)xanthine, 1-(5-hydroxyhexyl)-3-methyl-7-propylxanthine and 3-methyl-1-(5-oxohexyl)-7-propylxanthine (=propentofylline), and especially 3,7-dimethyl-1-(5-oxohexyl)xanthine (=pentoxifylline) may be included in the pharmaceutical product.

Particularly preferred compounds of the formula III for inclusion in this product are those compounds in which $R^5$ represents a methyl or ethyl group. Similarly preferred are those compounds of the formula III in which only one of the two radicals $R^4$ or $R^6$ represents the tertiary hydroxyalkyl group defined above. Additionally preferred are those compounds in which $R^7$ represents a methyl group, and n denotes an integer from 3 to 5, so that the tertiary hydroxyalkyl radical IIIa represents either [(ω-1)-hydroxy-(ω-1)-methyl]-pentyl, -hexyl or heptyl, especially those in which $R^5$ denotes methyl or ethyl.

Also worth particular mention are those compounds of formula III in which $R^4$ represents the tertiary hydroxyalkyl group, and $R^6$ represents hydrogen, alkyl, hydroxyalkyl or alkoxyalkyl, having 1 to 4 carbon atoms in each case, for example, 7-ethoxymethyl-1-(5-hydroxy-5-methylhexyl)-3-methylxanthine, 7-propyl-1-(5-hydroxy-5-methylhexyl)-3-methylxanthine, or 1-(5-hydroxy-5-methylhexyl)-3-methylxanthine.

As mentioned above some embodiments of the pharmaceutical product of the present invention may comprise the oxoalkylxanthines of the formula I and II, or the hydroxyalkylxanthines of the formula I and III, not as such but in the form of a prodrug from which the therapeutically active xanthine compounds, having the substituents defined in formulae I, II and III, can be released only by biotransformation in the body. Suitable derivatives include the acetalized oxoalkylxathines in which the carbonyl groups are replaced by the structural element of formula IV and the O-acylated hydroxyalkylxanthines having the structural element of the formula (V)

$$R^{11}-CO-O \qquad (V)$$

in place of the hydroxyl group, where $R^9$ and $R^{10}$ each represents an alkyl group having up to 4 carbon atoms or together represents an ethylene, trimethylene or tetramethylene group, and $R^{11}$ denotes an alkyl radical having up to 4 carbon atoms or optionally substituted phenyl or pyridyl.

In particular the preferred xanthine derivatives for inclusion in the pharmaceutical product of the present invention are pentoxifylline (3,7-dimethyl-1-(5-oxohexyl)xanthine), also known as TRENTAL, and 1-(5-hydroxy-5-methylhexyl)-3-methyl xanthine which is referred to hereafter as HWA 138.

The anti-TNF antibody or TNF binding fragment thereof included in the pharmaceutical product of the present invention is preferably a TNF neutralising antibody or antibody fragment. By neutralisation is intended the reduction in, or inhibition of a biological activity of TNF as measured by an in vitro or in vivo test.

The anti-TNF antibody or fragment included in the pharmaceutical product of the present invention may in general belong to any immunoglobulin class. Thus for example the anti-TNF antibody may be an immunoglobulin G or immunoglobulin M antibody.

The anti-TNF antibody may be of animal, for example mammalian origin and may be for example of murine, rat or human origin. The antibody may be a whole immunoglobulin, or a fragment thereof, for example a fragment derived by proteolytic cleavage of a whole antibody, such as F(ab')$_2$, Fab' or Fab fragments, or fragments obtained by recombinant DNA techniques, for example Fv fragments (as described in International Patent Application No. WO89/02465).

The anti-TNF antibody may be polyspecific but is preferably monospecific for human TNF. The antibodies may be polyclonal or monoclonal antibodies. Particularly useful antibodies for use according to the invention include recombinant anti-TNF antibodies and fragments thereof, i.e. anti-TNF antibodies or fragments which have been produced using recombinant DNA technqiues.

Especially useful recombinant antibodies include, (1) those having an antigen binding site at least part of which is derived from a different antibody, for example those in which hypervariable or complementarity determining regions of one antibody have been grafted into variable framework regions of a second, different, and preferably human, antibody (as described in European Patent Application EP-A-239400); (2) recombinant antibodies or fragments wherein non-Fv sequences have been substituted by non-Fv sequences from other, different antibodies (as described in European Patent Applications EP-A-171496, EP-A-173494 and EP-A-194276); or (3) recombinant antibodies or fragments possessing substantially the structure of a natural immunoglobulin but wherein the hinge region has a different number of cysteine residues from that found in the natural immunglobulin, or wherein one or more cysteine residues in a surface pocket of the recombinant antibody of fragment is in the place of another amino acid residue present in the natural immunoglobulin (as described in International Patent Applications Nos. WO89/01974 and WO89/01782 respectively).

The anti-TNF antibodies may be prepared using well-known immunological techniques employing TNF as antigen. Thus, for example, any suitable host may be injected with TNF and the serum collected to yield the desired polyclonal anti-TNF antibody after appropriate purification and/or concentration, (for example by affinity chromatography using immobilised TNF as the affinity medium). Alternatively, splenocytes or lymphocytes may be recovered from the TNF-injected host and immortalised using for example the method of Kohler et al, Eur. J. Immunol. 6, 511, (1976), the resulting cells being diluted and cloned to obtain a monoclonal line producing anti-TNF antibodies in accordance with conventional practice. Antibody fragments may be produced using conventional techniques, for example by enzymatic digestion of whole antibodies e.g. with pepsin [Parham, J. Immunol., 131, 2895, (1983)] or papain [Lamoyi and Nisonoff, J. Immunol. Meth., 56, 235, (1983)].

Where it is desired to produce recombinant anti-TNFα antibodies these may be produced using, for example, the general methods described in the above-mentioned patent specifications.

According to a second aspect of the invention there is provided the use of an antibody to TNF and of a xanthine derivative in the manufacture of a pharmaceutical product of the first aspect of the invention.

For example, an antibody to TNF and a xanthine derivative as described above may be mixed together and a pharmaceutically acceptable excipient, diluent, or carrier may optionally also be mixed in.

The pharmaceutical product may be utilised in any therapy where it is desired to reduce the level of TNF present in the human or animal body. The TNF may be in circulation in the body or present in an undesirably high level localised at a particular site in the body.

For example, elevated levels of TNF are implicated in immunoregulatory and inflammatory disorders and in septic, or endotoxic, and cardiovascular shock. The pharmaceutical product according to the first aspect of the present invention may be utilised in therapy of conditions which include sepsis, septic or endotoxic shock, cachexia, adult respiratory distress syndrome, AIDS, allergies, psoriasis, T.B., inflammatory bone disorders, blood coagulation disorders, burns, rejection episodes following organ or tissue transplant and autoimmune disease e.g. organ specific disease such as thyroiditis or non-specific organ diseases such as rheumatoid and osteo-arthritis.

Additionally, the pharmaceutical product may be used to ameliorate side effects associated with TNF generation during neoplastic therapy and also to eliminate or ameliorate shock related symptoms associated with the treatment or prevention of graft rejection by use of an antilymphocyte antibody, or may be used for treating multi-organ failure (MOF).

The pharmaceutical product according to the first aspect of the invention is preferably for treatment of sepsis, or septic/endotoxic shock.

The pharmaceutical product according to the first aspect of the invention may be for administration in any appropriate form and amount according to the therapy in which it is employed. It may be for prophylactic use, for example where circumstances are such that an elevation in the level of TNF might be expected or alternatively, the product may be for use in reducing the level of TNF after it has reached an undesirably high level or as the level is rising.

The pharmaceutical product may take any suitable form for administration, and, in particular, will be in a form suitable for parenteral administration e.g. by injection or infusion, for example by bolus injection or continuous infusion. Where the product is for injection or infusion it may take the form of a suspension, solution or emulsion of all or each of the components is an oily or aqueous vehicle and it may contain formulatory agents such as suspending, stabilising and/or dispersing agents.

Alternatively, the product may be in dry form, for reconstitution before use with an appropriate sterile liquid.

Where the anti-TNF and xanthine derivative components of the pharmaceutical product are for separate administration each may be formulated according to conventional practice and the formulation of each component may contain one or more other active ingredients.

In particular, while the anti-TNF antibody is likely to be unsuitable for oral administration such a limitation may not apply to the xanthine derivative.

When the xanthine derivative is for oral administration the formulation may contain, in addition, to the active ingredient, additives such as; starch—e.g. potato, maize or wheat starch or cellulose—or starch derivatives such as microcrystalline cellulose; silica; various sugars such as lactose; magnesium carbonate and/or calcium phosphate. It is desirable that, if the formulation is for oral administration it will be well tolerated by the patient's digestive system. To this end it may be desirable to include in the formulation mucus formers and resins. It may also be desirable to improve tolerance by formulating the xanthine derivative in a capsule which is insoluble in the gastric juices. It may also be preferable to include the xanthine derivative in a controlled release formulation.

In a still further aspect of the invention there is provided a method of treatment of a human or animal subject suffering from or at risk of a disorder associated with an undesirably high level of TNF, the method comprising administering to the subject an effective amount of the pharmaceutical product according to the first aspect of the invention. In particular the human or animal subject may be suffering from, or at risk from, sepsis, or septic or endotoxic shock.

The dose at which each pharmaceutical product will be administered will depend on the nature of the condition to be treated, the degree to which the TNF to be neutralised is, or is expected to be, raised above a desirable level, and on whether the product is being used prophylactically or to treat an existing condition. The dose will also be selected according to the age and condition of the patient.

Thus, for example, where the product is for treatment or prophylaxis of septic shock suitable doses of antibody to TNF lie in the range 0.001–30 mg/kg/day, preferably 0.01–10 mg/kg/day and particularly preferably 0.1–2 mg/kg/day while suitable doses of xanthine derivative lie in the range 0.5 to 100 mg/kg/day, preferably in the range from 0.5 to 50 mg/kg/day, and particularly preferably from 1 to 30 mg/kg/day. In general, the dose may be continued for as long as is necessary to alleviate the condition associated with the undesirably high level of TNF. In particular, it may be desirable to administer the dose of the xanthine derivative continuously by infusion or to repeat the dose of the xanthine derivative at regular, intervals for example of 2 to 24 hours, preferably 6 to 12 hours even if no repeat dose of anti-TNF antibody is administered.

BRIEF DESCRIPTION OF THE DRAWINGS

Embodiments of the invention are described below by way of example and with reference to the accompanying drawings of which.

Figure 2:
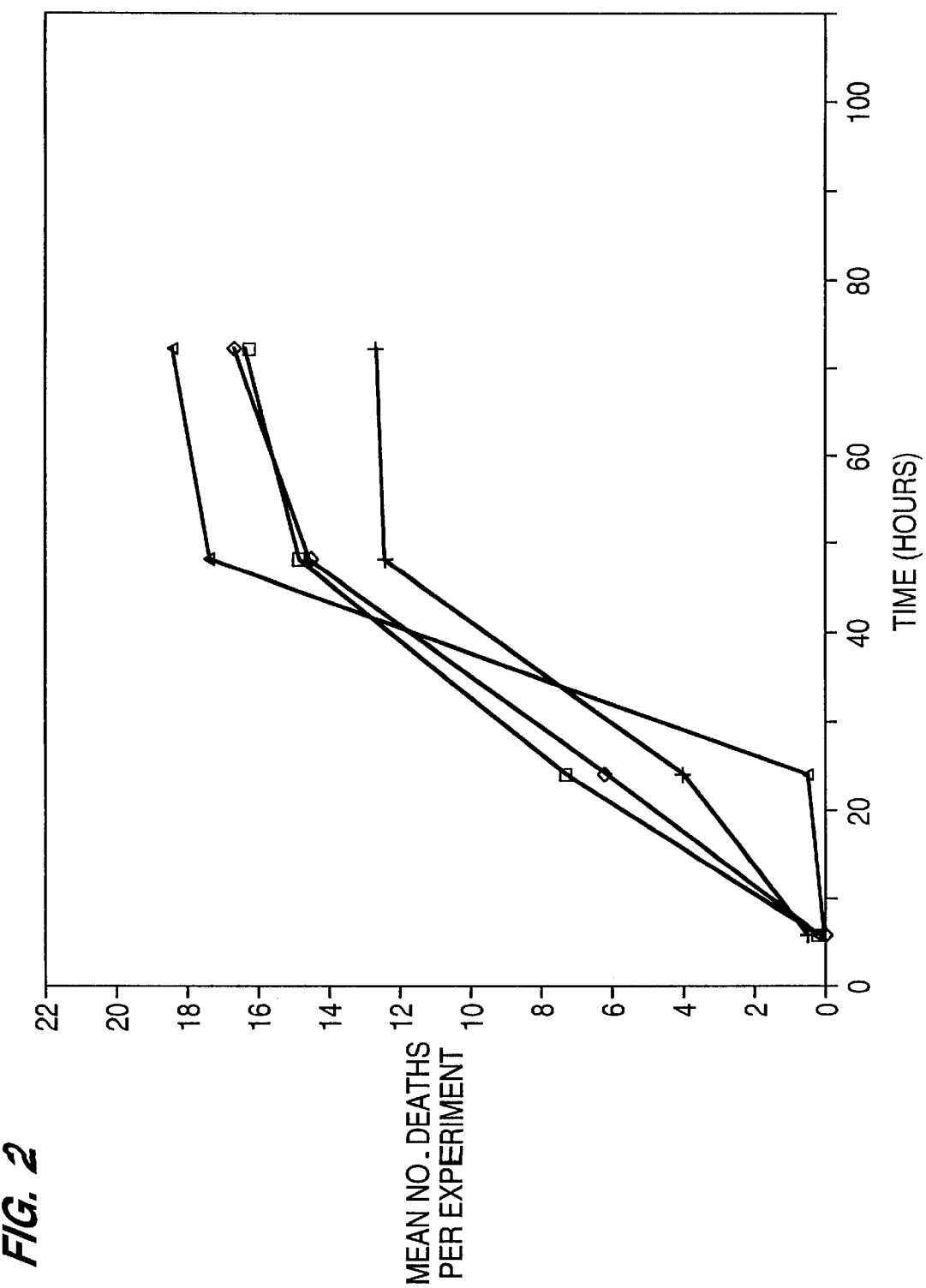
Figure 3:
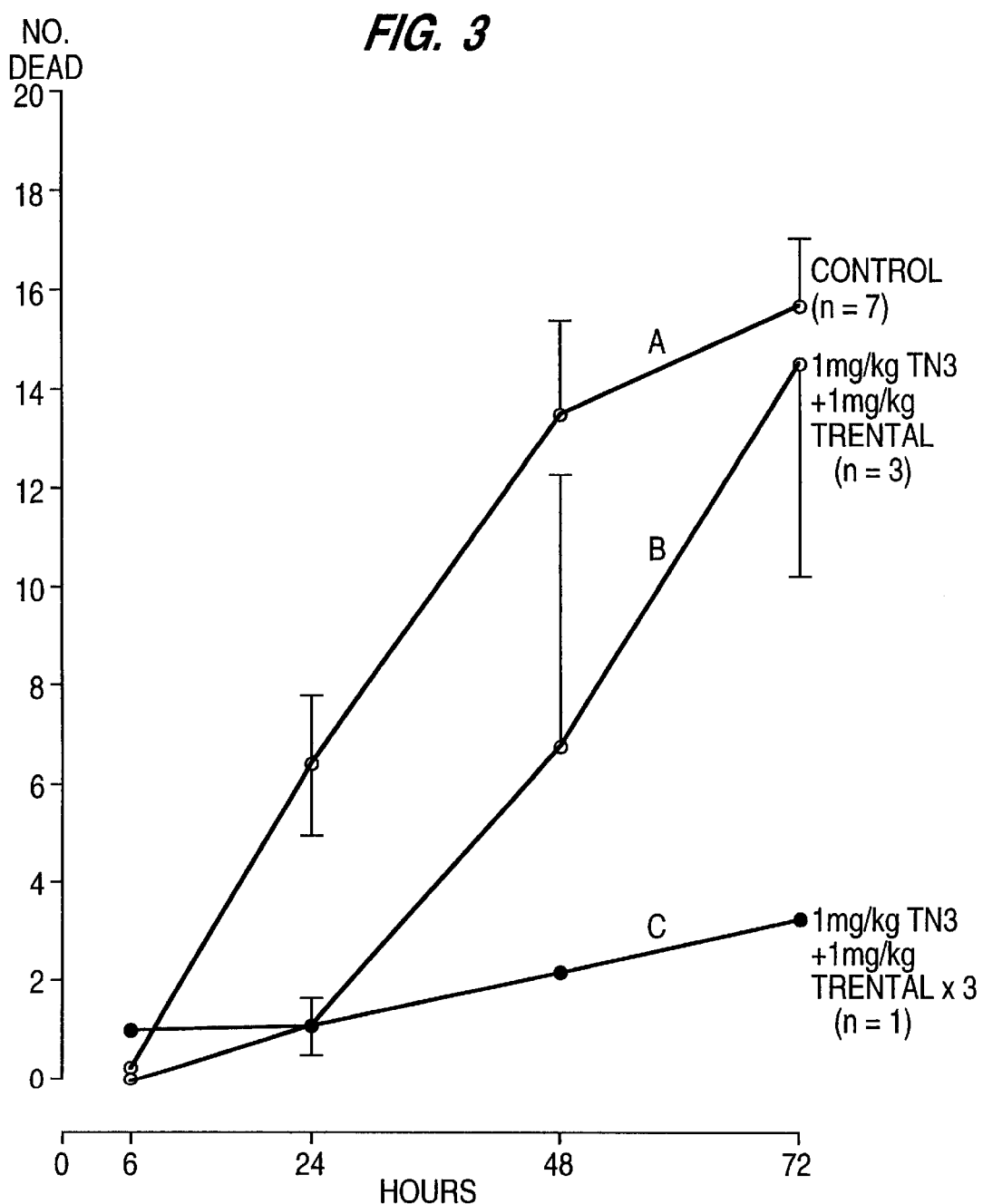

▽, pentoxifylline, 300 mg/kg; x, pentoxifylline, 10 mg/kg;

△, pentoxifylline, 1 mg/kg; □ control; +,TN3 19.12, 1 mg/kg;

◇ TN3 19.12, 30 mg/kg;

FIG. 2 shows a similar plot of mean deaths per experiment against time in an *E.coli* LPS induced shock model in which pentoxifylline and/or TN3 19.12 were administered to subjects at a dose of 1 mg/kg:

△ pentoxifylline, 1 mg/kg and TN3 19.12, 1 mg/kg;

◇ pentoxifylline alone 1 mg/kg; □; control; +, TN3, 19.12, 1 mg/kg;

FIG. 3 shows a similar plot to FIG. 2 in which mean deaths per experiment are plotted against time for an *E.coli* LPS induced shock model in which pentoxifylline and/or TN3 19.12 were administered to subjects at the following doses:

A—control, B—1 mg/kg pentoxifylline (single dose) and 1 mg/kg TN3 19.13, C—1 mg/kg pentoxifylline (dose repeated at 24, 48 and 72 hours) and 1 mg/kg TN3 19.13 (single dose)

Figure 4:
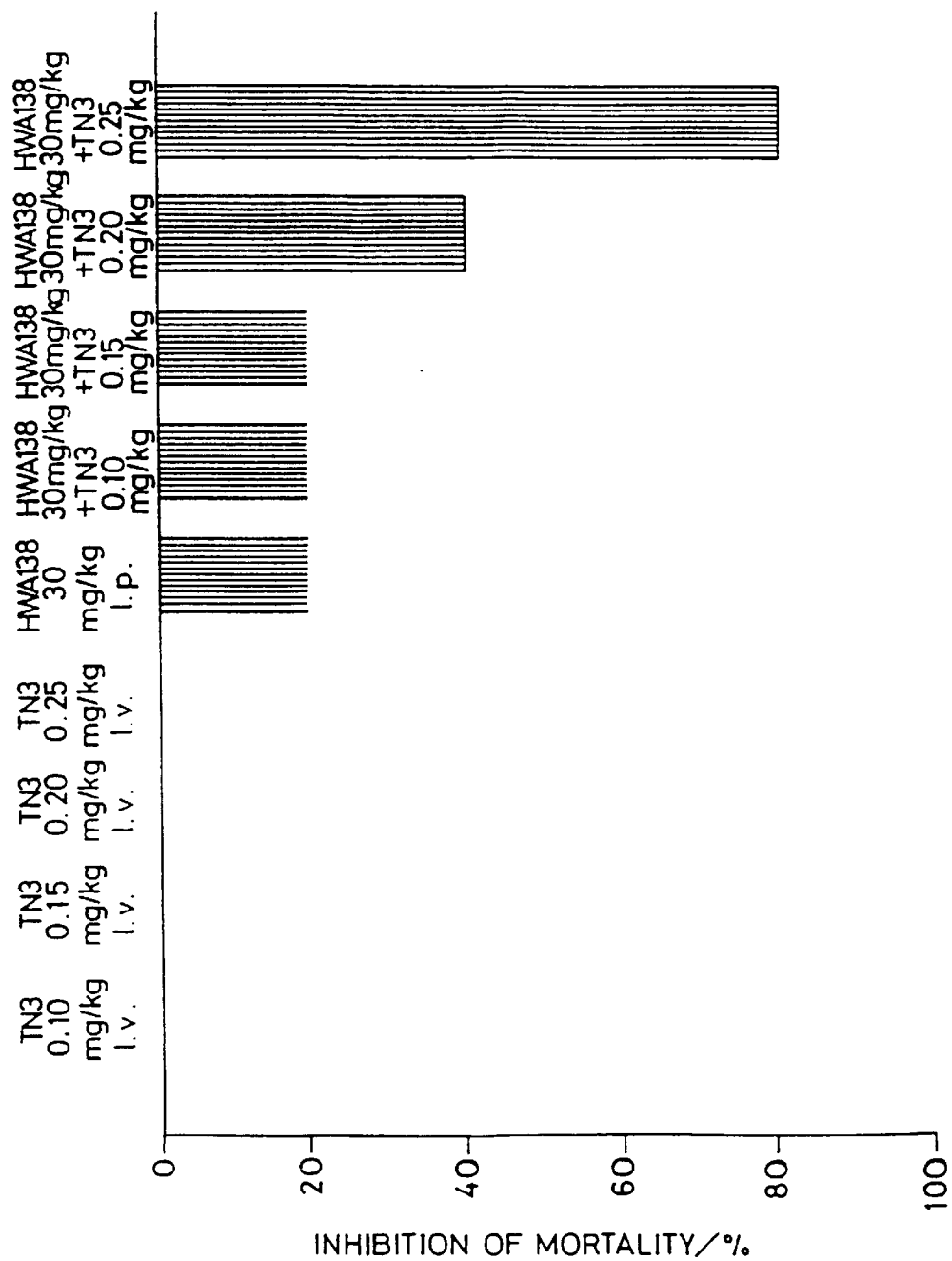

FIG. 4 shows a block diagram showing percentage inhibition of mortality in a *Salmonella abortus equi* LPS induced shock model in which various amounts of TN3 19.12 and/or xanthine derivative HWA 138 were administered to galactosamine sensitised and LPS challenged mice;

FIG. 5 shows a similar block diagram in which inhibition of mortality in a *salmonelia abortus equi* LPS induced shock model is plotted for an experiment in which various amounts of TN3 19.12 and/or the xanthine derivative pentoxifylline were administered to galactosamine sensitised and LPS challenged mice.

In the examples which follow bacterial LPS (lipopolysaccharide) was used to induce septic shock in mice.

DESCRIPTION OF EMBODIMENTS OF THE INVENTION

EXAMPLE 1

In a first experiment outbred mice were divided into groups and received treatment either with a hamster anti-murine TNF antibody TN3 19.12 or with the xanthine derivative, pentoxifylline.

Each group of animals received 60 mg/kg *E.coli* LPS by intravenous injection into a tail vein. This dose of LPS corresponds to the LD90 in mice.

Those groups of animals treated with TN3 19.12 received between 0.1 and 30 mg/kg of the antibody by intravenous injection of 0.1 ml of liquid into the tail vein 2 hours before LPS administration.

Those groups to be treated with pentoxifylline received between 1 mg/kg and 300 mg/kg intravenously five minutes prior to LPS administration.

In control experiments animals received an injection of an equivalent volume of saline.

Figure 1:
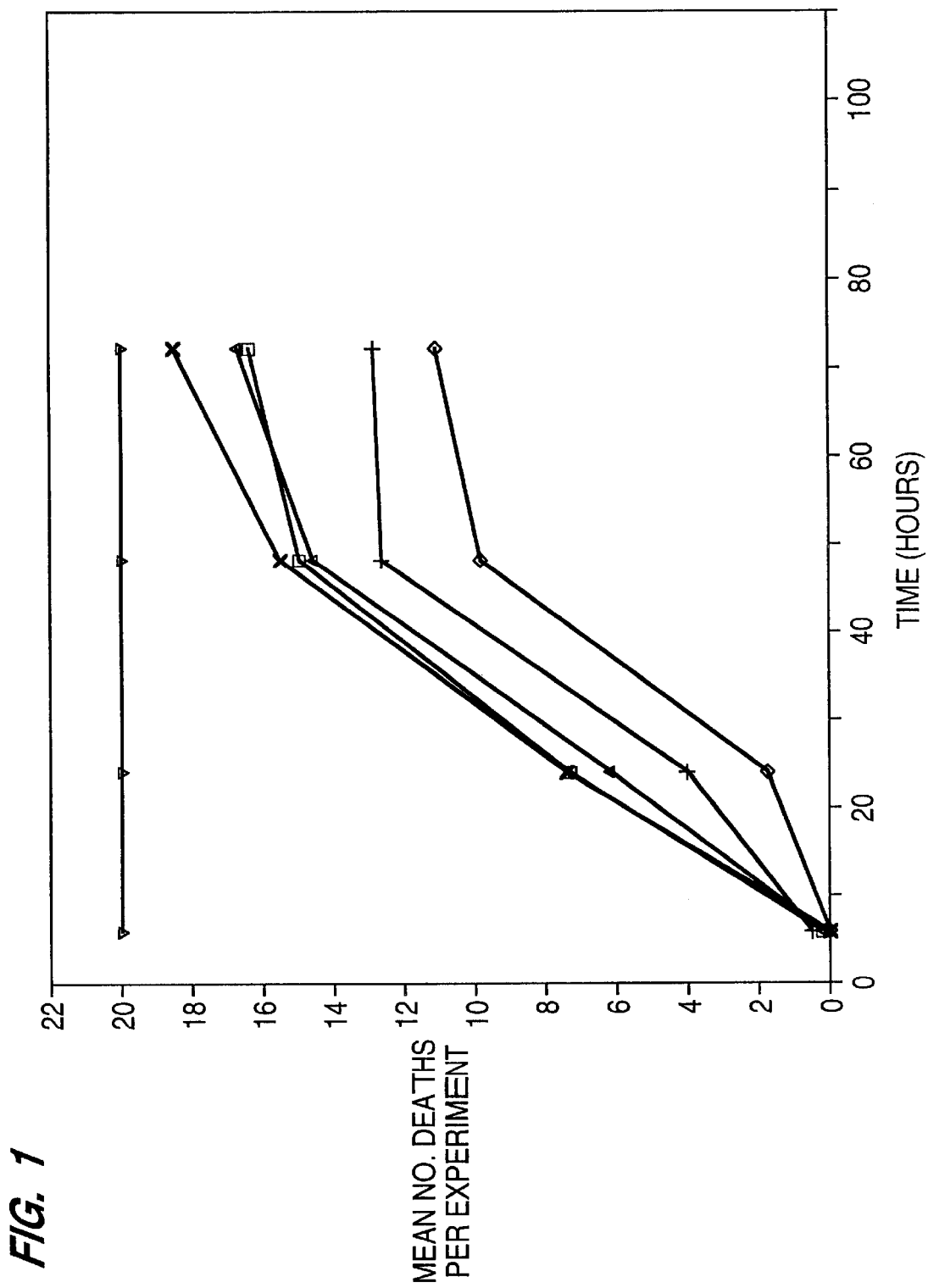
FIG. 1 shows a plot of mean deaths per experiment against time in an *E.coli* LPS induced shock model in which pentoxifylline or the hamster anti-mouse TNF antibody TN3 19.12 were administered to subjects of the experiment at various doses.

The results of these experiments are shown in FIG. 1. TN3 19.12 alone produced a protective effect at doses ≧1 mg/kg. By contrast, pentoxifylline alone had no effect at doses of 1 mg/kg and at higher concentrations it accelerated mortality.

In a second experiment both TN3 19.12 and pentoxifylline were administered at a dose of 1 mg/kg, the TN3 antibody being administered 2 hrs prior to LPS and the pentoxifylline 5 mins prior to LPS administration as before. The results are shown in FIG. 2 and demonstrate that mice receiving the combined treatment were protected against LPS induced death for 24 hrs after LPS administration. Subsequently, however, mortality rose to levels comparable with the control or pentoxifylline only groups.

It was believed that this effect may be due to the shorter half life of pentoxifylline relative to TN3 and might be compensated for by repeating pentoxifylline administration throughout the treatment period, for example, every 12 or 24 hours.

In order to confirm this hypothesis a further experiment was carried out with groups of twenty mice. The groups received one of three different treatment as follows:

A) Control—received 60 mg/kg *E.coli* LPS intravenously followed by saline injection;

B) Received 1 mg/kg TN3 19.12 i.v. 2 hrs prior to challenge with 60 mg/kg *E.coli* LPS i.v. and 1 mg/kg pentoxifylline i.v. 5 mins prior to challenge;

C) As B) but these mice also received repeat doses of 1 mg/kg pentoxifylline 24,48 and 72 hours after LPS challenge.

The results of this experiment are shown in FIG. 3. As in previous experiments group B) showed enhanced survival relative to the control at 24 hrs from LPS challenge but at later observation times survival was not significantly different from the control. By contrast the survival in group C) was markedly better than the control with 17 out of 20 animals surviving at 72 hrs from LPS challenge.

EXAMPLE 2

Similar experiments to those described above were carried out in galactosamine sensitised C57BL mice which were challenged with LPS from *Salmonella abortus equi*. Mortality was measured 96 hrs after the LPS challenge.

Low doses of TN3 of between 0.1 and 0.25 mg/kg administered intravenously 1 hr prior to administration of 0.2 μg LPS and 10 mg galactosamine per mouse had no protective effect. By contrast the xanthine derivative HWA 138 at a dose of 30 mg/kg intraperitoneally had a partially protective effect (c.20% inhibition of morality).

Coadministration of TN3 at doses ≧0.2 mg/kg together with 30 mg/kg HWA 138 significantly reduced mortality relative to 30 mg/kg HWA 138 used alone. These results are shown in FIG. 4.

This experiment was repeated using pentoxifylline in place of HWA 138 and similar results were obtained as shown in FIG. 5. In this case 100 mg/kg of pentoxifylline either alone or in combination with low doses of TN3 (0.10 or 0.15 mg/kg) had no protective effect. However, mortality could be completely inhibited by combined administered of 100 mg/kg pentoxifylline and 0.25 mg/kg of TN3.

We claim:

1. A pharmaceutical product comprising an antibody component and a xanthine derivative for use in treating conditions associated with elevated levels of TNF, wherein said antibody component is an antibody to TNF or an antigen-binding fragment thereof.

2. A pharmaceutical product according to claim 1, comprising a pharmaceutical composition comprising in admixture the antibody component and the xanthine derivative.

3. A pharmaceutical product according to claim 2, in which the ratio by weight of the xanthine derivative to the antibody component is in the range of 450 parts to 0.1 parts of xanthine derivative per 1 part of antibody component.

4. A pharmaceutical product according to claim 1, in which the xanthine derivative is a compound of formula I

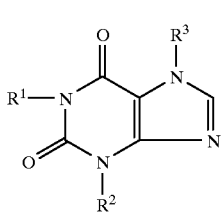

(I)

in which one of the radicals $R^1$ and $R^3$ represents a straight-chain alkyl, ($\omega$-1)-oxoalkyl or ($\omega$-1)-hydroxyalkyl group having 3 to 8 carbon atoms, and the two other radicals, $R^2$ and $R^3$ or $R^1$ and $R^2$, represent straight-chain or branched alkyl groups having 1 to 8 carbon atoms in the position of $R^1$ and $R^3$ and 1 to 4 carbon atoms in the position of $R^2$, where the total of carbon atoms in these two alkyl substituents does not exceed 10.

5. A pharmaceutical product according to claim 1, in which the xanthine derivative is a compound of formula II

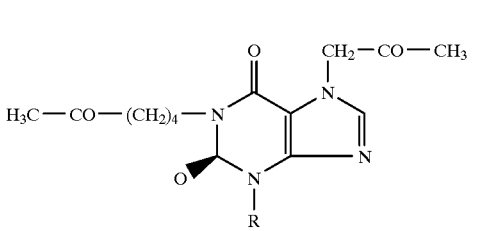

(II)

in which R represents an alkyl radical having 1 to 4 carbon atoms.

6. A pharmaceutical product according to claim 1, in which the xanthine derivative is a compound of formula III

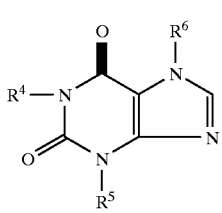

(III)

in which at least one of the radicals $R^4$ and $R^6$ represents a tertiary hydroxalkyl group of the formula IIIa

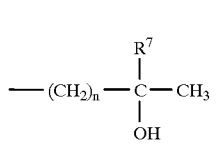

(IIIa)

wherein $R^7$ represents an alkyl group having up to 3 carbon atoms, and n is 2 3, 4 or 5 and wherein, if only one of the radicals $R^4$ and $R^6$ denotes such a tertiary hydroxyalkyl group of the formula IIIa, the other of $R^4$ or $R^6$ represents a hydrogen atom or an aliphatic hydrocarbon radical $R^8$ which has up to 6 carbon atoms and whose carbon chain is optionally interrupted at up to 2 points by a single oxygen atom or substituted by an oxo group or up to two hydroxyl groups, and $R^5$ represents an alkyl group having 1 to 4 carbon atoms.

7. A pharmaceutical product according to claim 4, in which the xanthine derivative is selected from the group consisting of:
1-hexyl-3,7-dimethylxanthine,
1-(5-hydroxyhexyl)-3,7-dimethylxanthine,
3,7-dimethyl-1-(5-oxohexyl)xanthine,
7-(5-hydroxyhexyl)-1,3-dimethylxanthine,
1,3-dimethyl-7-(5-oxohexyl)xanthine,
1,3-di-n-butyl-7-(2-oxopropyl)xanthine,
1,3-di-n-butyl-7-(3-3-oxobutyl)xanthine,
1-(5-hydroxyhexyl)-3-methyl-7-propylxanthine,
3-methyl-1-(5-oxohexyl)-7-propylxanthine and
3,7-dimethyl-1-(5-oxohexyl)xanthine.

8. A pharmaceutical product according to claim 6, in which the xanthine derivative is selected from the group consisting of:
7-ethoxymethyl-1-(5-hydroxy-5-methylhexyl)-3-methylxanthine, 7-propyl-1-(5-hydroxy-5-methylhexyl)-3-methylxanthine, and 1-(5-hydroxy-5-methylhexyl)-3-methylxanthine.

9. A pharmaceutical product according to claim 1, in which the antibody component is a TNF neutralizing antibody or an antigen binding fragment thereof.

10. A pharmaceutical product according to claim 1, in which the antibody component is monospecific.

11. A pharmaceutical product according to claim 1, in which the antibody component is a recombinant antibody or an antigen binding fragment thereof.

12. A pharmaceutical product according to claim 11, in which the antibody component is a humanized recombinant antibody or an antigen binding fragment thereof.

13. A pharmaceutical product according to claim 6, wherein $R^4$ represents a tertiary hydroxyalkyl group of the formula IIIa and $R^6$ is a hydrogen atom.

14. A pharmaceutical product according to claim 6, wherein $R^4$ represents a tertiary hydroxyalkyl group of the formula IIIa and $R^6$ is an aliphatic hydrocarbon radical $R^8$.

15. A pharmaceutical product according to claim 14, wherein said aliphatic hydrocarbon radical $R^8$ is substituted by an oxo group or up to two hydroxyl groups that are separated from the nitrogen atom to which the radical $R^8$ is attached by at least 2 carbon atoms.

16. A pharmaceutical product according to claim 14, wherein said aliphatic hydrocarbon radical $R^8$ is an alkyl group.

17. A pharmaceutical product according to claim 15, wherein said aliphatic hydrocarbon radical $R^8$ is a hydroxyalkyl group or an alkoxyalkyl group.

18. A pharmaceutical product according to claim 6, wherein $R^6$ represents a tertiary hydroxyalkyl group of the formula IIIa and $R^4$ is a hydrogen atom.

19. A pharmaceutical product according to claim 6, wherein $R^6$ represents a tertiary hydroxyalkyl group of the formula IIIa and $R^4$ is an aliphatic hydrocarbon radical $R^8$.

20. A pharmaceutical product according to claim 19, wherein said aliphatic hydrocarbon radical $R^8$ is substituted by an oxo group or up to two hydroxyl groups that are separated from the nitrogen atom to which the radical $R^8$ is attached by at least 2 carbon atoms.

21. A pharmaceutical product according to claim 19, wherein said aliphatic hydrocarbon radical $R^8$ is an alkyl group.

22. A pharmaceutical product according to claim 20, wherein said aliphatic hydrocarbon radical $R^8$ is a hydroxyalkyl group or an alkoxyalkyl group.

23. A pharmaceutical product according to claim 6, wherein $R^4$ and $R^6$ each independently represent a tertiary hydroxyalkyl group of the formula IIIa.

* * * * *

UNITED STATES PATENT AND TRADEMARK OFFICE
CERTIFICATE OF CORRECTION

PATENT NO. : 5,958,413
DATED : September 28, 1999
INVENTOR(S) : ANAGNOSTOPULOS et al.

It is certified that error appears in the above-identified patent and that said Letters Patent is hereby corrected as shown below:

On the title page, insert --[30] Foriegn Application Piority Data, November 1, 1990 [GB] United Kingdon 903783.5--

Signed and Sealed this

Twenty-fifth Day of April, 2000

Attest:

Attesting Officer

Q. TODD DICKINSON
Director of Patents and Trademarks